United States Patent [19]
Bescond et al.

[11] Patent Number: 5,973,149
[45] Date of Patent: Oct. 26, 1999

[54] PROCESS FOR PRODUCING THE EPSILON POLYMORPHIC FORM OF HEXANITROHEXAAZAISOWURTZITANE

[75] Inventors: Philippe Bescond, Saint Vrain; Hervé Graindorge, Vert le Petit; Hélène Mace, Villebon sur Yvette, all of France

[73] Assignee: SNPE, Paris, France

[21] Appl. No.: 09/168,413

[22] Filed: Oct. 8, 1998

[30] Foreign Application Priority Data

Oct. 29, 1997 [FR] France ................... 97 13546

[51] Int. Cl.$^6$ ................... C07D 487/16
[52] U.S. Cl. ................... 544/345
[58] Field of Search ................... 540/554, 475; 544/345

[56] References Cited

U.S. PATENT DOCUMENTS 5,693,794  12/1997  Nielsen ................... 540/554

FOREIGN PATENT DOCUMENTS 10-287675  10/1998  Japan .
WO9720785   6/1997  WIPO .
WO9827072   6/1998  WIPO .

OTHER PUBLICATIONS

Database WPI, Week 9506, Derwent Publications Ltd., London, GB; 1995.
AN 95–041279 XP002069511 and JP 06 321 962 A (Asahi Kasei Kogyo K.K. Nov. 22, 1995.
Chemical Abstracts, vol. 124, No. 24, Jun. 10, 1996 Columbus, OH; abstract No. 320923, XP002069506.
Y. Huang et al.:Proc. Beijing Int. Symp. Pyrotech. Explos., 3rd, 1995, pp. 167–169.
Chemical Abstracts, vol. 121, No. 22, Nov. 28, 1994, Columbus, OH; abstract No. 259139, XP002069507.
E. Von Holtz et al.: Propellants, Explos. Pyrotech., vol. 19, No. 4, 1994, pp. 206–212.
Chemical Abstracts, vol. 120, No. 20, May 16, 1994, Columbus, OH; abstract No. 248721, XP002069508.
F.M. Foltz et al.: Propellants, Explos., Pyrotech., vol. 19, No. 1, 1994, pp. 19–25.
Chemical Abstracts, vol. 124, No. 22, May 27, 1996, Columbus, OH; abstract No. 293607, XP002069509.
Z. Feng: Binggong Xuebao, Huohuangong Fence, vol. 18, No. 1, 1996, pp. 46–49.
Chemical Abstracts, vol. 118, No. 14, Apr. 5, 1993, Columbus, OH; abstract No. 132609, XP002069510.
T.P. Russel et al.: J. Phys. Chem., vol. 97, No. 9, 1993, pp. 1993–1997.
F.M. Foltz; Propellants, Explos., Pyrotech. 19, pp. 63–69 (1994) Thermal Stability of E–Hexanitrohexaazaisowurtzitane in an Estane Formulation.
F.M. Foltz; Propellants, Explos., Pyrotech. 19, pp. 19–25 (1994).
The Thermal Stability of the Polymorphs of Hexanitrohexaazaisowurtzitane, Part 1.
Proceedings of the American Defense Preparedness Assoc., Arnold T. Nielsen, Long Beach, CA; Queen Mary Hotel, Oct. 27–29, 1986.

*Primary Examiner*—Shailendra Kumar
*Attorney, Agent, or Firm*—Bucknam and Archer

[57] ABSTRACT

Process for producing the epsilon polymorphic form of hexanitrohexaazaisowurtzitane.

According to the process which is the subject-matter of the invention, a saturated solution of hexanitrohexaazaisowurtzitane of any polymorphic form is prepared in a mixture comprising a solvent chosen from esters, nitrites, ethers and ketones, except acetone, and a non-solvent chosen from aliphatic hydrocarbons and aromatic hydrocarbons, the solvent being more volatile than the non-solvent.

This saturated solution is subsequently seeded with a few crystals of hexanitrohexaazaisowurtzitane of epsilon polymorphic form and then the mixture is concentrated by evaporation of the solvent.

This process is simple, is economical and can be easily extrapolated to the industrial stage.

It makes it possible to obtain particle size fractions within the 10 $\mu$m–100 $\mu$m range with smooth grains with regular facies.

Hexanitrohexaazaisowurtzitane, in particular the densest epsilon form, is useful as oxidizing or explosive charge in pyrotechnic compositions.

11 Claims, No Drawings

PROCESS FOR PRODUCING THE EPSILON POLYMORPHIC FORM OF HEXANITROHEXAAZAISOWURTZITANE

FIELD OF THE INVENTION

The present invention relates to the production of the polymorphic form, known as the epsilon form, of hexanitrohexaazaisowurtzitane.

The invention lies in the field of powders, propellants and explosives which are very commonly used, in particular in the armaments industry.

BACKGROUND OF THE PRIOR ART

There have been many publications in recent years relating to 2,4,6,8,10,12-hexanitro-2,4,6,8,10,12-hexaazatetracyclo[5.5.0.0$^{5,9}$.0$^{3,11}$] dodecane, also known as hexanitrohexaazaisowurtzitane.

These publications describe the physical, chemical and detonating properties of this compound and/or various polymorphic forms, as well as its use in explosive compositions, propellants or powders for weapons.

Mention may be made, for example, of F. Foltz, who, in Propellants, Explosives, Pyrotechnics, 19, 63–69 (1994), studies the thermal stability of the epsilon polymorph in a poly(urethane-ester) and who, in Propellants, Explosives, Pyrotechnics, 19, 19–25 (1994), studies the thermal stability of the four polymorphic forms known as the alpha, beta, gamma and epsilon forms.

However, information relating to its synthesis is very rare, imprecise and insufficient for a person skilled in the art, even with his broad knowledge, to be able to prepare it.

While the writers of the abovementioned publications sometimes mention that the compound has been obtained from hexabenzylhexaazaisowurtzitane, they never describe how.

The most specific information relating to the synthesis appears in Patent Application PCT WO 97/20785, relating to the synthesis of tetraacetyldibenzylhexaazaisowurtzitane from hexabenzylhexaazaisowurtzitane.

It is mentioned therein that it is possible to obtain hexanitrohexaazaisowurtzitane from this intermediate acetylated compound by firstly reacting it with a nitrosating agent and then subsequently with a nitrating agent, but no example of such a reaction is disclosed and no details relating to the operating conditions (temperature, concentration of the acids, medium, and the like) are given.

Arnold T. Nielsen, at the Long Beach (Calif., U.S.A.) congress organized by the American Defense Preparedness Association and held at the Queen Mary Hotel on Oct. 27–29, 1986, also disclosed the synthesis of tetraacetyldibenzylhexaazaisowurtzitane by reaction of hexabenzylhexaazaisowurtzitane with acetic anhydride in the presence of hydrogen and of Pd/C as catalyst.

The writer also indicates that he had studied numerous operating conditions for the nitration of tetraacetyldibenzylhexaazaisowurtzitane with the aim of obtaining hexanitrohexaazaisowurtzitane but that this compound could never be obtained.

Despite this preconception and this imprecise information, operating conditions have now been found which make it possible to obtain hexanitrohexaazaisowurtzitane from tetraacetyldibenzylhexaazaisowurtzitane with an excellent yield. The hexanitrohexaazaisowurtzitane thus obtained exists in the alpha polymorphic form, with reference to the abovementioned publications by Foltz. Its density is 1.97 g/cm$^3$.

Now, according to the same publications by Foltz, it is the epsilon polymorphic form which has the highest density (2.04 g/cm$^3$) and which thus appears to be the most advantageous, in particular for the use thereof in pyrotechnic compositions.

While certain properties and characteristics of the epsilon form of hexanitrohexaazaisowurtzitane are known to a person skilled in the art, the information included within this actual state of the art, even complemented by the broad knowledge of a person skilled in the art, does not allow him to prepare it and to isolate it.

A person skilled in the art is thus in search of processes which make it possible to obtain this epsilon polymorphic form.

SUMMARY OF THE INVENTION

A first process for producing the epsilon polymorphic form has been discovered which consists, first of all, of mixing hexanitrohexaazaisowurtzitane of any polymorphic form, for example alpha, in a premix comprising:

20% to 40% by weight of a poly(glycidyl azide) corresponding to the general formula

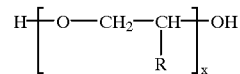

in which x is an integer such that 10≦x≦60 and R represents a (CH$_2$)$_n$N$_3$ or —CH$_2$—CHN$_3$—CH$_2$N$_3$ group in which n is an integer such that 1≦n≦5, 60% to 80% by weight of at least one tri-nitrate of a triol monomer comprising 3 to 12 carbon atoms, then subsequently carrying out at least one, preferably several and better still at least five thermal cycles of heating the mixture at a temperature of between 40° C. and 60° C. and then at a temperature of between 10° C. and 30° C., and then, finally, in removing the constituents of the premix by washing with an organic solvent.

When the hexanitrohexaazaisowurtzitane and the premix are mixed, a suspension of the hexanitrohexaazaisowurtzitane in the premix is obtained but a small portion is nevertheless dissolved.

Preferably, R represents —CH$_2$N$_3$ and x is such that 20≦x≦40.

Also preferably, the premix comprises 60% to 80% by weight of a mixture of trimethylolethane trinitrate and of 1,2,4-butanetriol trinitrate.

According to a preferred alternative form, this premix is composed of 27.5% by weight of poly(glycidyl azide), 35% by weight of trimethylolethane trinitrate, 35% by weight of 1,2,4-butanetriol trinitrate, 1.25% by weight of 2-nitrodiphenylamine and 1.25% by weight of N-methyl-para-nitroaniline.

Generally, according to this first process, the ratio by mass of the premix to the hexanitrohexaazaisowurtzitane to be recrystallized, respectively, is between 10 and 100.

A second process for producing the epsilon polymorphic form of hexanitrohexaazaisowurtzitane has been discovered which consists of preparing a saturated solution of hexanitrohexaazaisowurtzitane of any polymorphic form, for example alpha, in an acetone/toluene mixture, then seeding this saturated solution with a few crystals of hexanitrohexaazaisowurtzitane of epsilon polymorphic form, and then, finally, concentrating the solution by evaporation of the acetone.

This second process is much simpler to carry out, is more economical and can be more easily extrapolated to the industrial stage than the first one but it exhibits the disadvantage of only being able to provide products with a relatively large particle size which exist in the form of agglomerates, the median diameter of which is greater than 100 µm, generally between 100 µm and 180 µm, whatever the operating conditions envisaged, in particular the size of the seed crystals and the rate of evaporation of the acetone.

Now, the formulation of highly charged energetic materials generally requires the use, as pulverulent explosive charge, of several particle size fractions, in particular in the range from 10 µm to 100 µm, and preferably grains having smooth faces and a regular facies, and not agglomerates.

It is dangerous and economically highly damaging to mill the product obtained according to the second abovementioned process.

A person skilled in the art is thus in search of a process which makes it possible directly to obtain, without subsequent milling, various particle size fractions of the epsilon form of hexanitrohexaazaisowurtzitane with a well defined particle size, in particular particle size fractions having a median diameter of between approximately 10 µm and approximately 100 µm with, preferably, grains exhibiting smooth faces and a regular facies.

The present invention provides such a process.

It has been discovered, unexpectedly, that such results were achieved by carrying out the following reaction stages:

first of all, a saturated solution of hexanitrohexaazaisowurtzitane of any polymorphic form, preferably other than the epsilon form, for example alpha, is prepared in a mixture comprising, on one hand, an organic solvent for hexanitrohexaazaisowurtzitane chosen from the group consisting of esters, nitriles, ethers, ketones other than acetone, and their mixtures and, on the other hand, a non-solvent for hexanitrohexaazaisowurtzitane chosen from the group consisting of aliphatic hydrocarbons, aromatic hydrocarbons and their mixtures, the solvent for hexanitrohexaazaisowurtzitane being more volatile (lower boiling point) than the non-solvent and the solvent and the non-solvent being miscible in the proportions used, this saturated solution is subsequently seeded with a few crystals of hexanitrohexaazaisowurtzitane of epsilon polymorphic form, the solution is then concentrated by complete or partial evaporation of the solvent, which causes the appearance of crystals of hexanitrohexaazaisowurtzitane of epsilon polymorphic form, which remain in suspension in the mixture enriched in non-solvent and which can subsequently be recovered by any conventional means, such as filtration.

If the saturated solution comprises suspended hexanitrohexaazaisowurtzitane, it is preferable to remove this suspension, for example by filtration, before seeding, so as not to contaminate the final product obtained.

Furthermore, unexpectedly, it has been found that a product of higher purity is obtained, that is to say free in particular of other polymorphic forms of hexanitrohexaazaisowurtzitane, when, during the operation of concentrating the solution by evaporation of the organic solvent, the temperature does not exceed 50° C., that is to say when it is less than or equal to 50° C., for example between 10° C. and 50° C., preferably between 20° C. and 40° C.

Mention may be made, as examples of organic solvents for hexanitrohexaazaisowurtzitane which can be used according to the invention, of methyl formate, methyl acetate, ethyl acetate, isopropyl acetate, acetonitrile, ethyl acetate/acetonitrile mixtures, tetrahydrofuran (THF) and methyl ethyl ketone.

Mention may be made, as examples of non-solvents for hexanitrohexaazaisowurtzitane, of toluene, xylenes, alkanes, such as hexane, heptane and octane, and halogenated aliphatic hydrocarbons, in particular chlorinated aliphatic hydrocarbons, such as 1,2-dichloroethane.

According to a preferred alternative form, the solvent/non-solvent mixture comprises an organic solvent chosen from the group consisting of esters, preferably from the group consisting of formates and acetates, and a non-solvent chosen from the group consisting of alkanes, halogenated aliphatic hydrocarbons and aromatic hydrocarbons, preferably from the group consisting of aromatic hydrocarbons.

In a particularly preferred way, the solvent is chosen from the group consisting of methyl acetate, ethyl acetate and isopropyl acetate and the non-solvent is chosen from the group consisting of toluene and xylenes.

The ethyl acetate/toluene pair is particularly preferred.

Generally, the organic solvent/non-solvent ratio by volume is respectively between 10/90 and 50/50 and better still between 15/85 and 35/65.

According to another preferred alternative form, in order to prepare the saturated solution of hexanitrohexaazaisowurtzitane of any polymorphic form in the organic solvent/non-solvent mixture, firstly a saturated or unsaturated solution of hexanitrohexaazaisowurtzitane is prepared in the organic solvent or alternatively in the organic solvent and a portion of the non-solvent and, subsequently, the non-solvent or the remainder of the non-solvent is added. In addition to a simplification of the process, it has been found, unexpectedly, that finer particle sizes were thus obtained.

According to another preferred alternative form, the amount of seed represents between 0.2% and 5% by weight of the amount of hexanitrohexaazaisowurtzitane of any form to be recrystallized, preferably between 1% and 3% by weight.

The process according to the invention, which is simple to carry out, which is economical and which can be easily extrapolated to the industrial stage, in addition exhibits the considerable advantage of making it possible, by varying readily controllable experimental parameters, such as the particle size of the seed, the method of preparing the saturated solutions and the rate of evaporation of the solvent, to obtain any desired particle size fraction in the 10 µm-100 µm range, with grains generally having smooth faces and a regular facies.

While it is necessary with this process to have available beforehand, when it is employed for the very first time, a small amount of the desired product obtained according to another method, the very low proportion of seed necessary with respect to the product to be recrystallized subsequently renders the process completely autonomous.

The following non-limiting examples illustrate the invention and the advantages which it provides.

Examples 1 to 4 relate to the preparation of the starting material and of the seed which are necessary for carrying out the process according to the invention.

Furthermore, Example 4 is a comparative example which makes it possible to assess the advantages of the process according to the invention.

Examples 5 et seq. are examples representative of the process according to the invention.

EXAMPLE 1

Synthesis of Tetraacetyldibenzylhexaazaisowurtzitane 67 ml of dimethylformamide (DMF), 17 ml of acetic anhydride, 0.23 g (1.46 mmol) of bromobenzene, 20.8 g (29.4 mmol) of hexabenzylhexaazaisowurtzitane and 1.15 g of palladium hydroxide-on-charcoal (moisture: 50%, level of palladium in the dry material: 5%) are introduced, at room temperature (15–20° C.), into a 250 ml jacketed reactor equipped with a magnetic stirrer, a water-cooled reflux condenser and an introduction pipe equipped with a sinter for the introduction of hydrogen. After purging the equipment with an inert gas, the reaction mixture is brought from room temperature to 55° C. over 3 h, while introducing hydrogen into the mixture and while maintaining its pressure in the reactor at between $1.13 \times 10^5$ Pa and $1.25 \times 10^5$ Pa, and this temperature is then maintained for 2 h.

The introduction of hydrogen is halted and then 158 ml of acetic acid are introduced into the mixture, which is then brought to a temperature of between 80° C. and 90° C.

This mixture is filtered, in order to separate the catalyst, and then the filtrate is concentrated at 60° C.–70° C. under a reduced pressure of $2.5 \times 10^3$ Pa to $5 \times 10^3$ Pa (approximately 20 mm to 40 mm Hg).

After returning to room temperature, the residue is taken up in 100 ml of acetone. The tetraacetyldibenzylhexaazaisowurtzitane obtained, which has precipitated, is filtered off and rinsed with 50 ml of acetone.

After drying at 30° C. for 24 h under a reduced pressure of $5 \times 10^3$ Pa (approximately 40 mm Hg), 12.1 g (80% yield) of tetraacetyldibenzylhexaazaisowurtzitane, identified by conformity with reference spectra by mass, infrared and 60 MHz proton NMR spectrometry, are obtained.

EXAMPLE 2

Synthesis of Hexanitrohexaazaisowurtzitane of Alpha Polymorphic Form 313 g (3.37 mol) of liquid $N_2O_4$ are introduced, at 0° C., into a one liter jacketed reactor equipped with a mechanical stirrer and a temperature probe. 133 g (0.259 mol) of tetraacetyldibenzylhexaazaisowurtzitane obtained according to Example 1 are added between 0° C. and 50° C.

The temperature of the reaction mixture is allowed to rise to 15–16° C. (reflux of the $N_2O_4$) and then the mixture is left stirring and at reflux of the $N_2O_4$ for 20 h.

After having cooled the mixture to 0° C., 667 ml of a 20/80 by volume mixture of sulphuric acid and nitric acid respectively are added between 0° C. and 80° C., which corresponds to the addition of 12.8 mol of nitric acid.

Subsequently, the mixture is gradually heated, so as to remove the excess $N_2O_4$ by distillation, and then, when the temperature of the mixture reaches 73–75° C., the mixture is left stirring for 4 h.

After cooling to 40° C., the mixture is poured onto 2 l of a water/ice mixture. A solid separates by settling and is recovered by filtration and washing with hot water (40° C.) on a filter until the aqueous wash liquors are at neutral pH.

After drying, 104 g of hexanitrohexaazaisowurtzitane (97% yield) are obtained, a white solid identified by 200 MHz proton NMR in dimethyl sulphoxide (DMSO), by carbon NMR under the same conditions, by IR, by elemental analysis and by X-ray crystallographic study.

Its decomposition temperature is in the region of 247° C. and its purity can be estimated as greater than 95%.

Its density is 1.97 g/cm$^3$ from the X-ray crystallographic data.

The X-ray crystallographic study of a single crystal shows that this compound crystallizes with approximately 25 molar % of water and that it exhibits an orthorhombic crystalline structure with a Pbca space group having the following unit cell parameters: a=9.546 Å, b=13.232 Å, c=23.634 Å and Z=8.

Furthermore, the Fourier transform IR spectrum of a 1% dispersion in KBr exhibits, between 700 cm$^{-1}$ and 1200 cm$^{-1}$, the peaks characteristic of the alpha polymorphic form, with reference to the abovementioned publication by Foltz, Table 1, page 66. The peaks characteristic of the epsilon, beta and gamma forms are not observed.

The hexanitrohexaazaisowurtzitane obtained is thus found in the alpha polymorphic form.

EXAMPLE 3

Preparation of Hexanitrohexaazaisowurtzitane of Epsilon Polymorphic Form

Mixing Method

After suspending 0.5 g of hexanitrohexaazaisowurtzitane, obtained according to Example 2, at room temperature in the region of 20° C., with partial dissolution, in 15 g of a premix consisting of:

27.5% by weight of poly(glycidyl azide) (PAG) of formula

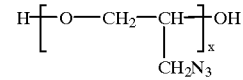

in which x is an integer such that $20 \leq x \leq 40$, sold by SNPE under the reference PAG-diol 1800 and for which the number-average molecular mass is in the region of 1800, 35% by weight of trimethylolethane trinitrate, 35% by weight of 1,2,4-butanetriol trinitrate, 1.25% by weight of 2-nitrodiphenylamine, 1.25% by weight of N-methyl-para-nitroaniline, six successive thermal cycles of 2h at 50° C. and then of 2h at 20° C. are carried out. Each cycle is thus composed of a period of heating the mixture from 20° C. to 50° C., of a period of maintaining the temperature at 50° C. for 2h, of a period of cooling the mixture from 50° C. to 20° C. and a period of maintaining the temperature at 20° C. for 2h.

The constituents of the premix are subsequently completely removed by washing on a filter with methylene chloride. 0.47 g of hexanitrohexaazaisowurtzitane, identified as according to Example 2, is collected.

Its density at 20° C. is 2.04 g/cm$^3$ from X-ray crystallographic data.

The X-ray crystallographic study of a single crystal shows that the product exhibits a monoclinic crystalline structure with a P2$_1$/n space group, the unit cell parameters of which are: a=8.864 Å, b=12.581 Å, c=13.388 Å and Z=4.

Furthermore, the Fourier transform IR spectrum of a 1% dispersion in KBr exhibits, between 700 cm$^{-1}$ and 1200 cm$^{-1}$, the peaks characteristic of the epsilon polymorphic form, with reference to the abovementioned Foltz publication, Table 1, page 66. The peaks characteristic of the alpha, beta and gamma forms are not observed. The hexanitrohexaazaisowurtzitane obtained is thus found in the epsilon polymorphic form.

It has been found, by optical microscopy, that the size of the grains is of the order of 150 μm.

EXAMPLE 4

Preparation of Hexanitrohexaazaisowurtzitane of Epsilon Polymorphic Form

Method by Seeding in Acetone/Toluene Medium 10 g of hexanitrohexaazaisowurtzitane obtained according to Example 2 are mixed, at room temperature in the region of 20° C., with 20 ml of acetone. A saturated solution is thus obtained in which a small portion of the starting hexanitrohexaazaisowurtzitane remains in suspension.

80 ml of toluene are added, which makes it possible to obtain a saturated solution of hexanitrohexaazaisowurtzitane in a 20/80 by volume acetone/toluene mixture respectively, in which solution a small portion of the starting hexanitrohexaazaisowurtzitane remains in suspension.

This suspension is filtered and the filtrate, that is to say the saturated solution, is collected and subsequently seeded with a few crystals of hexanitrohexaazaisowurtzitane of epsilon polymorphic form obtained according to Example 3.

The mixture is subsequently concentrated at 25° C. under a partial pressure of $2.5 \times 10^3$–$5 \times 10^3$ Pa (approximately 20–40 mm Hg), until all the acetone has been removed.

A white solid (9 g) precipitates during this concentration operation and is recovered by filtration.

This white solid, identified and analysed as described in Example 3, which exhibits all the characteristics, in particular physical and spectral, of the product obtained in Example 3, is hexanitrohexaazaisowurtzitane of epsilon polymorphic form exhibiting a median diameter of approximately 150 $\mu$m.

This example was repeated, on one hand by using seeds of various particle sizes between 15 $\mu$m and 80 $\mu$m, obtained by milling the seed used with ultrasound, and, on the other hand, by varying the rate of evaporation of the acetone.

The characterization of the morphology of the grains by optical microscopy shows that the grains obtained are always agglomerates with a diameter greater than 100 $\mu$m and that the particle size of the seed has little influence on the final particle size.

EXAMPLES 5 TO 16

Preparation According to the Invention of Various Particle Size Fractions of Hexanitrohexaazaisowurtzitane of Epsilon Polymorphic Form in Ethyl Acetate/Toluene Medium The examples on the laboratory scale (20 g or 30 g approximately) were carried out in a jacketed glass laboratory reactor with a volume of 250 ml or 500 ml, depending on the examples, equipped with a mechanical paddle stirrer, a temperature probe, a distillation column with a system for regulating the degree of reflux surmounted by a reflux condenser at –20° C. and a dry ice trap, and a receptacle for collecting the condensates.

The examples on the pilot scale (approximately 3.5 kg) were carried out in a 60 l stainless steel jacketed reactor comprising the same type of equipment.

EXAMPLES 5 TO 11

Preparation of a Particle Size Fraction Having a Median Diameter of Between 20 $\mu$m and 40 $\mu$m

EXAMPLE 5

30 g of hexanitrohexaazaisowurtzitane of alpha polymorphic form obtained according to Example 2 are dissolved, at room temperature in the region of 20° C., in 90 ml of ethyl acetate and then 210 ml of toluene are added. A saturated solution of hexanitrohexaazaisowurtzitane in an ethyl acetate/toluene 30/70 respectively by volume mixture is thus obtained.

This solution is subsequently seeded with 0.6 g of hexanitrohexaazaisowurtzitane (2% with respect to the starting material) of epsilon polymorphic form obtained according to Example 3, milled beforehand with ultrasound and exhibiting a median diameter of between 5 $\mu$m and 10 $\mu$m (determination by optical microscopy), and then the solution is concentrated by evaporation of the ethyl acetate with stirring at 150 revolutions/min under a partial pressure of $6.25 \times 10^3$ Pa (approximately 50 mm Hg) provided by means of a liquid ring pump and a control valve and at room temperature of approximately 20° C.

The degree of reflux is adjusted so as to distil approximately 90% of the initial ethyl acetate over approximately 3 h.

A white solid (27.5 g) precipitates during this concentration operation and is recovered by filtration (90% yield).

This white solid, identified and analysed as described in Examples 3 and 4, which exhibits all the characteristics, in particular physical and spectral, of the product obtained in these Examples 3 and 4, is hexanitrohexaazaisowurtzitane of epsilon polymorphic form exhibiting a median diameter of between 20 $\mu$m and 40 $\mu$m (determination by optical microscopy).

The grains exhibit smooth faces and a regular facies (observation by optical microscopy).

EXAMPLES 6 TO 9

Example 5 was repeated on the pilot scale from 3.5 kg of hexanitrohexaazaisowurtzitane of alpha polymorphic form obtained according to Example 2.

The variations in experimental conditions and the results obtained are as follows:

|  | Example 6 | Example 7 | Example 8 | Example 9 |
|---|---|---|---|---|
| Ethyl acetate/toluene ratio by volume | 34/66 | 30/70 | 30/70 | 30/70 |
| Median diameter of the seed(*) | 10 $\mu$m | 8 $\mu$m | 8 $\mu$m | 8 $\mu$m |
| Duration of the concentration | 3 h 35 min | 2 h 30 min | 2 h 30 min | 2 h 15 min |
| Yield | 88.3% | 90.3% | 91.3% | 92% |
| Median diameter of the product recovered(*) | 30 $\mu$m | 30 $\mu$m | 34 $\mu$m | 35 $\mu$m |

(*)particle size by laser diffraction

EXAMPLES 10 AND 11

Example 5 was repeated but with 0.3 g (1%) of seed for Example 10 and 1.2 g (4%) for Example 11.

The same results are obtained as in Example 5.

EXAMPLES 12 TO 15

Preparation of a Particle Size Fraction Having a Median Diameter of Between 40 $\mu$m and 60 $\mu$m

EXAMPLE 12

30 g of hexanitrohexaazaisowurtzitane of alpha polymorphic form obtained according to Example 2 are mixed, at ambient temperature of approximately 20° C., with a mixture of 120 ml of ethyl acetate and 180 ml of toluene.

A saturated solution is obtained in which a small portion of the starting hexanitrohexaazaisowurtzitane remains in suspension. This suspension is filtered and the filtrate, that is to say the saturated solution, is collected and subsequently seeded with 0.6 g of hexanitrohexaazaisowurtzitane of epsilon polymorphic form obtained according to Example 4, milled beforehand with ultrasound and exhibiting a median diameter of between 10 μm and 15 μm.

The solution is concentrated by evaporating the ethyl acetate under the same conditions as in Example 5 but halting the distillation after having evaporated 80% of the starting ethyl acetate (duration approximately 3 h).

26 g (85% yield) of hexanitrohexaazaisowurtzitane of epsilon polymorphic form are recovered exhibiting, on one hand, a median diameter of between 40 μm and 60 μm and, on the other hand, smooth faces and a regular facies.

EXAMPLES 13 AND 14

Example 12 was repeated but concentrating the solution at a temperature of 40° C. in Example 13 and 75° C. in Example 14.

In Example 13, the same results are obtained as in Example 12.

In Example 14, the product obtained is a mixture of the epsilon and gamma polymorphic forms of hexanitrohexaazaisowurtzitane and exists in the form of needles and of agglomerates.

EXAMPLE 15

Example 12 was repeated but from 30 g of hexanitrohexaazaisowurtzitane of epsilon polymorphic form (instead of the alpha form) obtained according to Example 4.

The same results are obtained as in Example 12.

EXAMPLE 16

Preparation of a Particle Size Fraction Having a Median Diameter of Between 80 μm and 100 μm Example 12 was repeated but with a seed exhibiting a median diameter of between 25 μm and 40 μm.

The hexanitrohexaazaisowurtzitane of epsilon polymorphic form recovered (87% yield) exhibits a median diameter of between 80 μm and 100 μm.

EXAMPLES 17 TO 23

Preparation According to the Invention of Various Particle Size Fractions Within the 5 μm–100 μm Range of Hexanitrohexaazaisowurtzitane of Epsilon Polymorphic Form, in Various Solvent/Non-solvent Media The same equipment is used as in Examples 5 to 16.

EXAMPLE 17

In Isopropyl Acetate/Toluene 30/70 by Volume Respectively Medium 20 g of hexanitrohexaazaisowurtzitane of alpha polymorphic form obtained according to Example 2 are mixed, at room temperature of 20° C., with a mixture of 60 ml of isopropyl acetate and 140 ml of toluene. A saturated solution is obtained in which a small portion of the starting hexanitrohexaazaisowurtzitane remains in suspension. This suspension is filtered and the filtrate is collected and seeded with 0.4 g (2%) of hexanitrohexaazaisowurtzitane of epsilon polymorphic form obtained according to Example 4, milled beforehand with ultrasound and exhibiting a median diameter of approximately 5 μm.

The solution is concentrated by evaporation of the isopropyl acetate under the same experimental conditions as in Example 5.

Hexanitrohexaazaisowurtzitane of epsilon polymorphic form, exhibiting, on one hand, a median diameter of between 5 μm and 10 μm and, on the other hand, non-agglomerated grains of regular shape, is recovered with a yield of 92%.

EXAMPLE 18

In Methyl Acetate/Toluene 30/70 by Volume Respectively Medium

Example 17 was repeated using methyl acetate instead of isopropyl acetate and a seed with a median diameter of 13 μm instead of 5 μm.

The hexanitrohexaazaisowurtzitane of epsilon polymorphic form, recovered with a yield of 92%, exhibits a median diameter of 10 μm to 15 μm.

EXAMPLE 19

In Methyl Acetate/1,2-dichloroethane 30/70 by Volume Respectively Medium

Example 17 was repeated using ethyl acetate instead of isopropyl acetate and 1,2-dichloroethane instead of toluene.

The hexanitrohexaazaisowurtzitane of epsilon polymorphic form recovered (51% yield) exists in the form of clusters having a median diameter of approximately 15 μm.

EXAMPLE 20

In Ethyl Acetate/Xylene 30/70 by Volume Respectively Medium

Example 19 was repeated using ortho-xylene instead of 1,2-dichloroethane.

The hexanitrohexaazaisowurtzitane of epsilon polymorphic form recovered (92% yield) exists in the form of regular grains having a median diameter of 20 μm to 25 μm.

EXAMPLE 21

In THF/Toluene 22/78 by Volume Respectively Medium

Example 17 was repeated using a mixture of 44 ml of THF and 156 ml of toluene.

The hexanitrohexaazaisowurtzitane of epsilon polymorphic form recovered (92% yield) exists in the form of agglomerates having a median diameter of 60 μm to 70 μm.

EXAMPLE 22

In Acetonitrile/Ethyl Acetate/Toluene 21/5/74 by Volume Respectively Medium

Example 17 was repeated using a mixture of 42 ml of acetonitrile, 10 ml of ethyl acetate and 148 ml of toluene.

Hexanitrohexaazaisowurtzitane of epsilon polymorphic form, existing in the form of agglomerates having a median diameter of approximately 80 μm, is recovered with a yield of 77%.

EXAMPLE 23

In Methyl Ethyl Ketone/Toluene 20/80 by Volume Respectively Medium

Example 17 was repeated using a mixture of 40 ml of methyl ethyl ketone and 160 ml of toluene.

Hexanitrohexaazaisowurtzitane of epsilon polymorphic form, existing in the form of agglomerates having a median diameter of approximately 80 μm, is recovered with a yield of 92%.

We claim:

1. Process for producing the epsilon polymorphic form of hexanitrohexaazaisowurtzitane, characterized in that:

a saturated solution of hexanitrohexaazaisowurtzitane of any polymorphic form is prepared in a mixture comprising, on one hand, an organic solvent for hexanitrohexaazaisowurtzitane chosen from the group consisting of esters, nitrites, ethers, ketones, with the exception of acetone, and their mixtures and, on the other hand, a non-solvent for hexanitrohexaazaisowurtzitane chosen from the group consisting of aliphatic hydrocarbons, aromatic hydrocarbons and their mixtures, the solvent for hexanitrohexaazaisowurtzitane being more volatile than the non-solvent, this saturated solution is seeded with a few crystals of hexanitrohexaazaisowurtzitane of epsilon polymorphic form, the solution is subsequently concentrated by evaporation of the solvent.

2. Process according to claim 1, characterized in that the mixture comprises an organic solvent chosen from the group consisting of esters and a non-solvent chosen from the group consisting of alkanes, halogenated aliphatic hydrocarbons and aromatic hydrocarbons.

3. Process according to claim 2, characterized in that the mixture comprises an organic solvent chosen from the group consisting of formates and acetates and a non-solvent chosen from the group consisting of aromatic hydrocarbons.

4. Process according to claim 3, characterized in that the organic solvent is an acetate chosen from the group consisting of methyl acetate, ethyl acetate and isopropyl acetate and in that the non-solvent is an aromatic hydrocarbon chosen from the group consisting of toluene and xylenes.

5. Process according to claim 4, characterized in that the organic solvent is ethyl acetate and in that the non-solvent is toluene.

6. Process according to claim 1, characterized in that the solvent/non-solvent ratio by volume is respectively between 10/90 and 50/50.

7. Process according to claim 1, characterized in that the amount of seed represents between 0.2% and 5% by weight of the amount of hexanitrohexaazaisowurtzitane of any polymorphic form.

8. Process according to claim 1, characterized in that, during the operation of concentrating the solution by evaporation of the solvent, the temperature does not exceed 50° C.

9. Process according to claim 1, characterized in that, firstly, a solution of hexanitrohexaazaisowurtzitane of any polymorphic form is prepared in the organic solvent or in the organic solvent and a portion of the non-solvent and in that, subsequently, the non-solvent or the remainder of the non-solvent is added.

10. The process according to claim 8 wherein said epsilon polymorphic form of hexanitrohexaazaisowurtzitane has a median diameter between 10 μm and 100 μm.

11. The process according to claim 10 wherein said polymorphic form of hexanitrohexaazaisowurtzitane has grains which exhibit smooth faces and a regular facies.

* * * * *

UNITED STATES PATENT AND TRADEMARK OFFICE
CERTIFICATE OF CORRECTION

PATENT NO. : 5,973,149
DATED : OCTOBER 26, 1999
INVENTOR(S) : PHILIPPE BESCOND, ET AL

It is certified that error appears in the above-indentified patent and that said Letters Patent is hereby corrected as shown below:

The error to be corrected is the word "nitrites" which must be changed to "nitriles". This error is found in the Abstract, line 4 below the title;

claim 1, column 11, line 12.

Signed and Sealed this

Twenty-third Day of May, 2000

Attest:

Q. TODD DICKINSON

*Attesting Officer*      *Director of Patents and Trademarks*